(12) United States Patent
Ettori et al.

(10) Patent No.: US 7,890,170 B2
(45) Date of Patent: *Feb. 15, 2011

(54) RATE ABERRANT BEAT SELECTION AND TEMPLATE FORMATION

(75) Inventors: Benjamin Ettori, Pittsburgh, PA (US); Joseph M. Bocek, Seattle, WA (US); Jaeho Kim, Redmond, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/838,626

(22) Filed: Jul. 19, 2010

(65) Prior Publication Data

US 2010/0280400 A1 Nov. 4, 2010

Related U.S. Application Data

(63) Continuation of application No. 11/608,411, filed on Dec. 8, 2006, now Pat. No. 7,765,002.

(51) Int. Cl.
*A61N 1/00* (2006.01)
(52) U.S. Cl. .................................................. 607/14
(58) Field of Classification Search ................. 600/510; 607/14
See application file for complete search history.

(56) References Cited

U.S. PATENT DOCUMENTS

| | | | |
|---|---|---|---|
| 4,407,288 A | 10/1983 | Langer et al. |
| 4,452,248 A | 6/1984 | Keller, Jr. |
| 4,589,420 A | 5/1986 | Adams et al. |
| 5,000,189 A | 3/1991 | Throne et al. |
| 5,010,888 A | 4/1991 | Jadvar et al. |
| 5,497,780 A | 3/1996 | Zehender |
| 5,560,368 A | 10/1996 | Berger |
| 5,779,645 A | 7/1998 | Olson et al. |
| 5,795,303 A | 8/1998 | Swanson et al. |
| 5,817,133 A | 10/1998 | Houben |
| 6,223,078 B1 | 4/2001 | Marcovecchio |
| 6,266,554 B1 | 7/2001 | Hsu et al. |

(Continued)

FOREIGN PATENT DOCUMENTS

WO WO-2008/073266 A2 6/2008

(Continued)

OTHER PUBLICATIONS

"U.S. Appl. No. 10/291,200, Notice of Allowance mailed Nov. 10, 2005", 9 pgs.

(Continued)

*Primary Examiner*—Niketa I Patel
*Assistant Examiner*—Robert N Wieland
(74) *Attorney, Agent, or Firm*—Schwegman, Lundberg & Woessner, P.A.

(57) ABSTRACT

A cardiac rhythm management system can be used to detect episode beats associated with cardiac events in a subject's body. These events may be monitored and depolarization morphology information can be derived for candidate arrhythmic beats in an arrhythmia episode. An arrhythmic beat morphology template may be formed from selecting at least one of the candidate arrhythmic beats based upon user's labeling according to specific morphologies of one or more candidate episodes. Methods of use are also presented.

20 Claims, 9 Drawing Sheets

U.S. PATENT DOCUMENTS

| | | | |
|---|---|---|---|
| 6,275,732 B1 | 8/2001 | Hsu et al. | |
| 6,308,095 B1 | 10/2001 | Hsu et al. | |
| 6,312,388 B1 | 11/2001 | Marcovecchio et al. | |
| 6,370,431 B1 | 4/2002 | Stoop et al. | |
| 6,434,417 B1 | 8/2002 | Lovett | |
| 6,449,503 B1 | 9/2002 | Hsu | |
| 6,480,734 B1 | 11/2002 | Zhang et al. | |
| 6,708,058 B2 | 3/2004 | Kim et al. | |
| 6,728,572 B2 | 4/2004 | Hsu et al. | |
| 6,745,068 B2 | 6/2004 | Koyrakh et al. | |
| 6,760,615 B2 | 7/2004 | Ferek-Petric | |
| 6,766,190 B2 | 7/2004 | Ferek-Petric | |
| 6,889,081 B2 | 5/2005 | Hsu | |
| 7,031,764 B2 | 4/2006 | Schwartz et al. | |
| 7,085,599 B2 | 8/2006 | Kim et al. | |
| 7,415,307 B2 | 8/2008 | Sharma et al. | |
| 7,539,536 B2 | 5/2009 | Schwartz et al. | |
| 7,765,002 B2 | 7/2010 | Benjamin et al. | |
| 2002/0032469 A1 | 3/2002 | Marcovecchio | |
| 2002/0087091 A1 | 7/2002 | Koyrakh et al. | |
| 2002/0091333 A1 | 7/2002 | Hsu et al. | |
| 2002/0183637 A1 | 12/2002 | Kim et al. | |
| 2002/0183639 A1 | 12/2002 | Sweeney et al. | |
| 2003/0083586 A1 | 5/2003 | Ferek-Petric | |
| 2003/0083587 A1 | 5/2003 | Ferek-Petric | |
| 2003/0100923 A1 | 5/2003 | Bjorling et al. | |
| 2003/0181818 A1 | 9/2003 | Kim et al. | |
| 2004/0093035 A1 | 5/2004 | Schwartz et al. | |
| 2004/0127806 A1 | 7/2004 | Sweeney | |
| 2004/0176694 A1 | 9/2004 | Kim et al. | |
| 2004/0243014 A1* | 12/2004 | Lee et al. | 600/510 |
| 2005/0137485 A1 | 6/2005 | Cao et al. | |
| 2005/0192506 A1 | 9/2005 | Kim et al. | |
| 2006/0074331 A1 | 4/2006 | Kim et al. | |
| 2006/0111643 A1 | 5/2006 | Cazares et al. | |
| 2006/0111747 A1 | 5/2006 | Cazares et al. | |
| 2006/0155201 A1 | 7/2006 | Schwartz et al. | |
| 2006/0217621 A1 | 9/2006 | Kim et al. | |
| 2006/0281998 A1 | 12/2006 | Li | |
| 2007/0142737 A1 | 6/2007 | Cazares et al. | |
| 2008/0140143 A1 | 6/2008 | Ettori et al. | |
| 2009/0216289 A1 | 8/2009 | Schwartz et al. | |

FOREIGN PATENT DOCUMENTS

| | | | |
|---|---|---|---|
| WO | WO-2008/073266 A3 | 6/2008 | |

OTHER PUBLICATIONS

"U.S. Appl. No. 10/291,200, Preliminary Amendment and Response filed Aug. 18, 2005 to Restriction Requirement mailed Jul. 18, 2005", 16 pgs.

"U.S. Appl. No. 10/291,200, Restriction Requirement mailed Jul. 18, 2005", 5 pgs.

"U.S. Appl. No. 11/277,095, Response filed Nov. 4, 2008 to Non-Final Office Action mailed Aug. 4, 2008", 15 pgs.

"U.S. Appl. No. 11/277,095, Non-Final Office Action mailed Aug. 4, 2008", 16 pgs.

"U.S. Appl. No. 11/277,095, Notice of Allowance mailed Jan. 21, 2009", 7 pgs.

"U.S. Appl. No. 11/608,411, Non-Final Office Action mailed Dec. 26, 2008", 5 pgs.

"U.S. Appl. No. 11/608,411, Notice of Allowance mailed Mar. 22, 2010", 7 pgs.

"U.S. Appl. No. 11/608,411, Advisory Action mailed Oct. 21, 2009", 3 pgs.

"U.S. Appl. No. 11/608,411, Final Office Action mailed Jul. 17, 2009", 6 pgs.

"U.S. Appl. No. 11/608,411, Response filed Mar. 26, 2009 to Non-Final Office Action mailed Dec. 26, 2008", 14 pgs.

"U.S. Appl. No. 11/608,411, Response filed Sep. 17, 2009 to Final Office Action mailed Jul. 17, 2009", 11 pgs.

"U.S. Appl. No. 11/608,411, Response filed Nov. 16, 2009 to Advisory Action mailed Oct. 21, 2009", 12 pgs.

"International Application Serial No. PCT/US2007/024975, International Search Report mailed Jun. 27, 2008", 3 pgs.

"International Application Serial No. PCT/US2007/024975, Written Opinion mailed Jun. 27, 2008", 7 pgs.

Cazares, S., et al., "Arrhythmia Discrimination Based on Determination of Rate Dependency", U.S. Appl. No. 11/312,280, filed Dec. 20, 2005, 41 pgs.

Duru, Firat, et al., "The Potential for Inappropriate Ventricular Tachycardia Confirmation Using the Intracardiac Electrogram (EGM) Width Criterion", *PACE*, vol. 22, (Jul. 1999), 1039-1046.

Grady, T. A., et al., "Prognostic Significance of Exercise-Induced Left Bundle-Branch Block", JAMA, 279(2), (1998), 153-156.

Horowitz, L. N., et al., "Epicardial and Endocardial Activation During Sustained Ventricular Tachycardia in Man", *Circulation*, 61(6), (1980), 1227-1238.

Kinoshita, S., et al., "Transient Disappearance of Complete Right Bundle Branch (BBB) During Exercise", *Journal of Electrocardiology*, 29(3), (1996), 255-256.

* cited by examiner

RATE ABERRANT BEAT SELECTION AND TEMPLATE FORMATION

CLAIM OF PRIORITY

This application is a continuation of and claims the benefit of priority under 35 U.S.C. §120 to U.S. application Ser. No. 11/608,411, filed Dec. 8, 2006, now issued as U.S. Pat. No. 7,765,002, which is hereby incorporated by reference in its entirety.

TECHNICAL FIELD

This document relates generally to cardiac rhythm management (CRM) systems and particularly, but not by way of limitation, to cardiac rhythm management systems and methods that use information about a patient's prior tachyarrhythmia episodes to create one or more templates for discriminating between different heart rhythms.

BACKGROUND

When functioning properly, the human heart maintains its own intrinsic rhythm. Its sinoatrial node generates an intrinsic electrical cardiac signal that depolarizes the atria. Such atrial depolarizations cause atrial heart contractions. Its atrioventricular node then passes the intrinsic cardiac signal to depolarize the ventricles. Such ventricular depolarizations cause ventricular heart contractions. These intrinsic cardiac signals can be sensed on a surface electrocardiogram (e.g., a "surface ECG signal") obtained from electrodes placed on the patient's skin, or from electrodes implanted within the patient's body (e.g., an "electrogram signal"). The surface ECG and electrogram waveforms generally include artifacts associated with atrial depolarizations ("P-waves") and those associated with ventricular depolarizations ("QRS complexes").

When people have irregular cardiac rhythms, referred to as cardiac arrhythmias, or poor spatial coordination of heart contractions, diminished blood circulation may result. For such persons, a cardiac rhythm management (CRM) system may be used to improve these conditions. CRM systems include, among other things, pacers which deliver timed sequences of low energy electrical stimuli, called pace pulses, to the heart. By properly timing the delivery of pace pulses, the heart can be induced to contract in proper rhythm, improving blood pumping efficiency. Another type of CRM system includes defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, which include abnormal heart rhythms that are typically characterized by a rapid heart rate. Tachyarrhythmias generally include supraventricular tachyarrhythmia (SVT), such as atrial tachyarrhythmia (AT), and ventricular tachyarrhythmia (VT). Tachyarrhythmia can also include fibrillation, such as ventricular fibrillation (VF), which is characterized by an irregular heart rhythm.

In a normal heart, the sinoatrial node, the heart's predominant natural pacemaker, generates electrical impulses, called action potentials. The action potentials propagate through an electrical conduction system to the atria and then to the ventricles of the heart to excite the myocardial tissues. The atria and ventricles normally contract in atrio-ventricular sequence and synchrony to result in efficient blood-pumping. VT typically occurs when the electrical impulses propagate along a pathologically formed self-sustaining conductive loop within the ventricles, or when a natural pacemaker in a ventricle usurps control of the heart rate from the sinoatrial node. When the contractions of the atria and the ventricles become dissociated during VT, the ventricles may contract before they are properly filled with blood, resulting in diminished blood flow throughout the body. This condition can become life-threatening, such as when the brain is deprived of sufficient oxygen supply.

Cardioversion and defibrillation can be used to terminate most tachyarrhythmias, including AT, VT, and VF. An implantable cardioverter/defibrillator (ICD) is a CRM device that delivers an electric shock to terminate a detected tachyarrhythmia episode by depolarizing the entire myocardium simultaneously and rendering it refractory. Another type of electrical therapy for tachyarrhythmia is anti-tachyarrhythmia pacing (ATP). In ATP, the heart is competitively paced in an effort to interrupt the reentrant loop causing the tachyarrhythmia. An ICD can include ATP and defibrillation capabilities so that ATP is delivered to the heart when a non-fibrillation VT is detected, while a defibrillation shock is delivered when VF occurs.

The efficacy of cardioversion, defibrillation, and ATP in terminating a tachyarrhythmia can depend on the type and origin of the tachyarrhythmia. An unnecessary shock delivered during a non-life-threatening tachyarrhythmia episode may cause substantial pain in the patient, and reduces the longevity of the ICD while providing the patient with little or no benefit. On the other hand, a necessary therapy that is improperly withheld during a life-threatening tachyarrhythmia episode may result in irreversible harm to the patient, including death.

OVERVIEW

Cardiac depolarization morphology templates can allow effective delivery of an appropriate therapy by comparing sensed cardiac signals to a previously stored morphology template. For these and other reasons, there is a need for improved techniques of establishing or using one or more morphology templates, such as for discriminating between SVTs and VTs.

A significant proportion of inappropriate shocks are associated with a condition known as rate aberrancy. Patients with rate aberrancy can experience a change in conduction pathway during SVT (e.g., rate dependent bundle branch block). This can frustrate morphology-based tachyarrhythmia discrimination techniques. One method of addressing rate aberrancy is to use information about a patient's prior tachyarrhythmia episode or episodes to improve SVT/VT discrimination. This will help promote an appropriate choice of therapy to be applied in response to a patient's later tachyarrhythmia episodes.

In Example 1, a method includes monitoring an intrinsic electrical cardiac signal, deriving depolarization morphology information for candidate arrhythmic beats in an arrhythmia episode of the intrinsic electrical cardiac signal, selecting at least one of the candidate arrhythmic beats for use in forming an arrhythmic beat morphology template representative of the episode, the selecting including using information obtained from comparing at least one of a beat morphology, a cardiac cycle interval, a beat amplitude, and a rate zone classification of a candidate arrhythmic beat to respective information about the beat morphology, the cardiac cycle interval, the beat amplitude, and the rate zone classification of at least one other selected candidate arrhythmic beat from the arrhythmia episode, and forming the arrhythmic beat morphology template from depolarization morphology information of at least one of the selected candidate arrhythmic beats.

In Example 2, the method of Example 1 optionally includes determining a similarity between depolarization morphology information of a post-episode beat and the arrhythmic beat morphology template and classifying the post-episode beat as a function of the determined similarity.

In Example 3, the method of Examples 1 or 2 optionally includes selecting at least one arrhythmia episode to be used for the selecting at least one of the candidate arrhythmic beats and the forming the arrhythmic beat morphology template, wherein the selecting at least one arrhythmia episode comprises using a physician classification of an arrhythmia type of the arrhythmia episode.

In Example 4, the method of Examples 1-3 optionally includes performing an automatic classification of an arrhythmia type of the arrhythmia episode, obtaining a physician classification of the arrhythmia type of the arrhythmia episode, and comparing the physician classification to the automatic classification in determining whether to select the at least one arrhythmia episode to be used for the selecting at least one of the candidate arrhythmic beats and the forming the arrhythmic beat morphology template.

In Example 5, the method of Examples 1-4 are optionally configured such that the automatic classification of the arrhythmia type includes using at least first and second classification criteria, and comprising using information about which of the first and second classification criteria contributed to the automatic classification in determining whether to select the at least one arrhythmia episode to be used for the selecting at least one of the candidate arrhythmic beats and the forming the arrhythmic beat morphology template.

In Example 6, the method of Examples 1-5 optionally includes pre-selecting one or more particular beats, within the arrhythmia episode, to be used as the candidate arrhythmic beats to be used in forming an arrhythmic beat morphology template representative of the episode.

In Example 7, the method of Examples 1-6 are optionally configured such that the pre-selecting comprises selecting one or more beats that were used in performing an automatic classification of the arrhythmia type.

In Example 8, the method of Examples 1-7 are optionally configured such that the pre-selecting comprises selecting one or more beats that were associated with a decision to apply therapy.

In Example 9, the method of Examples 1-8 are optionally configured such that the pre-selecting comprises selecting one or more beats associated with an onset of the arrhythmia episode.

In Example 10, the method of Examples 1-9 are optionally configured such that the pre-selecting comprises selecting one or more beats that are deemed morphologically different from a normal sinus rhythm (NSR) morphology.

In Example 11, the method of Examples 1-10 optionally includes ordering at least two arrhythmia episodes to be used in the forming the arrhythmic beat morphology template.

In Example 12, the method of Examples 1-11 are optionally configured such that the ordering comprises prioritizing the at least two arrhythmia episodes in the forming the arrhythmic beat morphology template wherein the prioritizing uses at least one of a time of occurrence, a diagnostic classification, an episode origin and an average heart rate.

In Example 13, the method of Examples 1-12 optionally includes confirming episode classification by comparing the arrhythmic beat morphology template to at least one stored arrhythmia episode.

In Example 14, the method of Examples 1-13 optionally includes confirming viability of the arrhythmic beat morphology template by comparing the arrhythmic beat morphology template to depolarization morphology information of arrhythmic beats in at least one arrhythmia episode.

In Example 15, the method of Examples 1-14 are optionally configured such that the confirming viability of the beat morphology template includes comparing beats within the arrhythmic beat morphology template.

In Example 16, the method of Examples 1-15 optionally includes reforming the arrhythmic beat morphology template using depolarization morphology information of arrhythmic beats after eliminating at least one outlier from the arrhythmic beats.

In Example 17, the method of Examples 1-16 optionally includes reforming the arrhythmic beat morphology template using depolarization morphology information of subsequent arrhythmic beats.

In Example 18, the method of Examples 1-17 optionally includes displaying the arrhythmic beat morphology template to a user.

In Example 19, a system includes means for monitoring an intrinsic electrical cardiac signal, means for deriving depolarization morphology information for candidate arrhythmic beats in an arrhythmia episode of the intrinsic electrical cardiac signal, means for selecting at least one of the candidate arrhythmic beats for use in forming an arrhythmic beat morphology template representative of the episode, the selecting including using information obtained from comparing at least one of a cardiac cycle interval, a beat amplitude, and a rate zone classification of a candidate arrhythmic beat to respective information about the cardiac cycle interval, the beat amplitude, and the rate zone classification of at least one other selected candidate arrhythmic beat from the arrhythmia episode, and means for forming the arrhythmic beat morphology template by combining depolarization morphology information of at least two of the selected candidate arrhythmic beats.

In Example 20, a system includes an intrinsic electrical cardiac signal sensing circuit, a depolarization morphology storage circuit, coupled to the sensing circuit. The depolarization morphology storage may be configured for storing depolarization morphology information for candidate arrhythmic beats occurring in an arrhythmia episode of a patient. A processor circuit, coupled to the depolarization morphology storage circuit, may include an arrhythmic beat morphology template and a candidate arrhythmic beat selector circuit. The candidate arrhythmic beat selector circuit may be configured to select at least one of the candidate arrhythmic beats for use in forming the arrhythmic beat morphology template representative of the episode. The selection criteria of the candidate arrhythmic beat selector circuit may include using information obtained from comparing at least one of a cardiac cycle interval, a beat amplitude, and a rate zone classification of a candidate arrhythmic beat to respective information about the cardiac cycle interval, the beat amplitude, and the rate zone classification of at least one other selected candidate arrhythmic beat from the arrhythmia episode. Comparison of other characteristics of two or more candidate arrhythmic beats from the episode are also possible, any combination of which may provide an improved selector circuit. Additionally, a beat morphology aggregator circuit, coupled to form the arrhythmic beat morphology template may combine depolarization morphology information of at least two of the selected candidate arrhythmic beats to the arrhythmic beat morphology template.

In Example 21, the system of Example 20 optionally includes a beat morphology comparator circuit comprised with the processor circuit and configured to determine an indication of a similarity between depolarization morphology information of a post-episode beat and the arrhythmic beat morphology template. The beat morphology comparator circuit, according to this example, is also adapted to classify the post-episode beat as a function of the determined similarity.

In Example 22, the system of Examples 20-21 optionally includes an arrhythmia episode selection circuit comprised with the processor circuit and configured to select at least one arrhythmia episode to be used in the candidate arrhythmic beat selector circuit and the beat morphology aggregator circuit, wherein the arrhythmia episode selection circuit is adapted to receive input derived from a physician classification of an arrhythmia type of the arrhythmia episode.

In Example 23, the system of Examples 20-22 optionally includes an automatic arrhythmia classification circuit comprised with the processor circuit and adapted to form an automatic classification of an arrhythmia type of the arrhythmia episode selected by the arrhythmia episode selection circuit using input derived from a received physician classification of an arrhythmia type of the arrhythmia episode. The automatic arrhythmia classification circuit, according to this example, is also configured to compare the physician classification to the automatic classification in determining whether to select the at least one arrhythmia episode to be used by the arrhythmia episode selection circuit and beat morphology aggregator circuit.

In Example 24, the system of Examples 20-23 optionally includes a pre-selection circuit comprised with the processor circuit and adapted to pre-select one or more particular beats, within the arrhythmia episode, to be used as the candidate arrhythmic beats in the formation of an arrhythmic beat morphology template representative of the episode.

In Example 25, the system of Examples 20-24 are optionally configured such that the pre-selection circuit is configured to select one or more beats that were used in performing an automatic classification of the arrhythmia type.

In Example 26, the system of Examples 20-25 are optionally configured such that the pre-selection circuit is configured to select one or more beats associated with an onset of the arrhythmia episode.

In Example 27, the system of Examples 20-26 are optionally configured such that the pre-selection circuit is configured to select one or more beats that are deemed morphologically different from a normal sinus rhythm (NSR) morphology.

In Example 28, the system of Examples 20-28 is optionally configured such that the beat morphology aggregator circuit is configured to order at least two arrhythmia episodes to be used in the forming the arrhythmic beat morphology template.

In Example 29, the system of Examples 20-28 is optionally configured such that the beat morphology aggregator circuit is adapted to confirm viability of the arrhythmic beat morphology template by comparing the arrhythmic beat morphology template to depolarization morphology information of arrhythmic beats in at least one arrhythmia episode.

In Example 30, the system of Examples 20-29 are optionally configured such that the beat morphology aggregator circuit is adapted to reform the arrhythmic beat morphology template using depolarization morphology information of arrhythmic beats after eliminating at least one outlier from the arrhythmic beats.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present systems and methods may be used in applications involving implantable medical devices ("IMDs") including, but not limited to, implantable cardiac rhythm management ("CRM") systems such as pacers, cardioverters/ defibrillators, pacers/defibrillators, biventricular or other multi-site resynchronization or coordination devices such as cardiac resynchronization therapy ("CRT") devices, patient monitoring systems, neural modulation systems, and drug delivery systems. In addition, the systems and methods described herein may also be employed in unimplanted devices, including but not limited to, external pacers, cardioverters/defibrillators, pacer/defibrillators, biventricular or other multi-site resynchronization or coordination devices, monitors, programmers and recorders, whether such devices are used for providing sensing, receiving, prediction processing, or therapy.

Introduction

SVTs and VTs are associated with abnormal heart rhythms characterized by a rapid heart rate. As discussed above, subjects with rate aberrancy can experience a change in conduction pathway during SVT (e.g., rate dependent bundle branch block). This can frustrate morphology-based tachyarrhythmia discrimination techniques. Subjects having rate aberrancy can experience inappropriate anti-tachyarrhythmia therapy delivery as a result of increased difficulty in discriminating between SVT and VT when morphology based rhythm discrimination is used.

Figure 1:
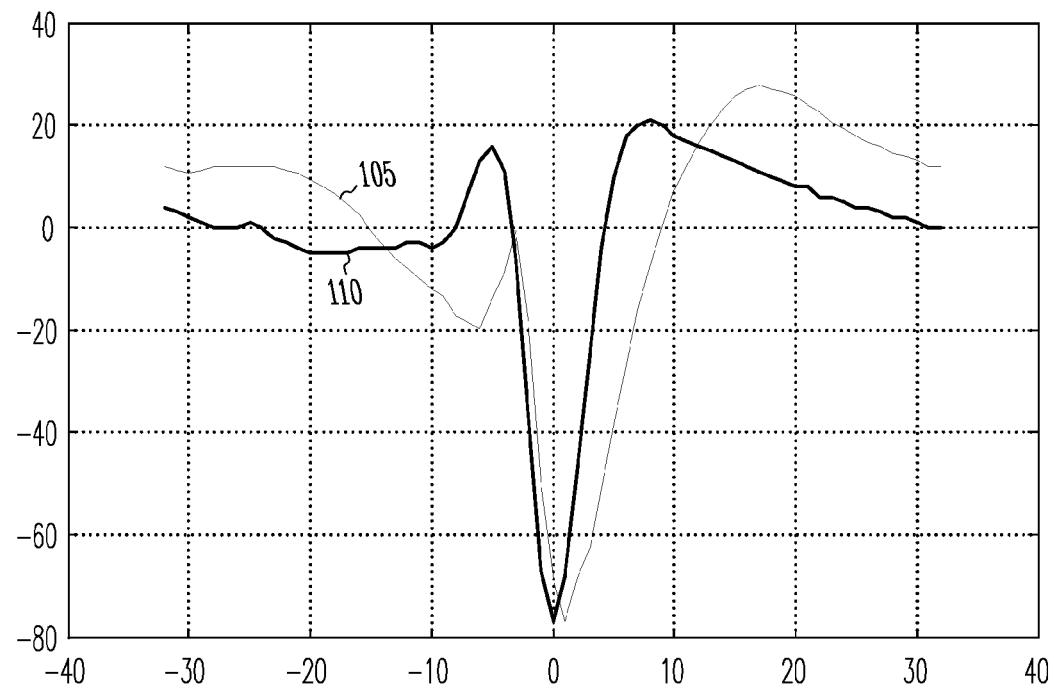
FIG. 1 illustrates an effect of a rate aberrant signal morphology.
Figure 2:
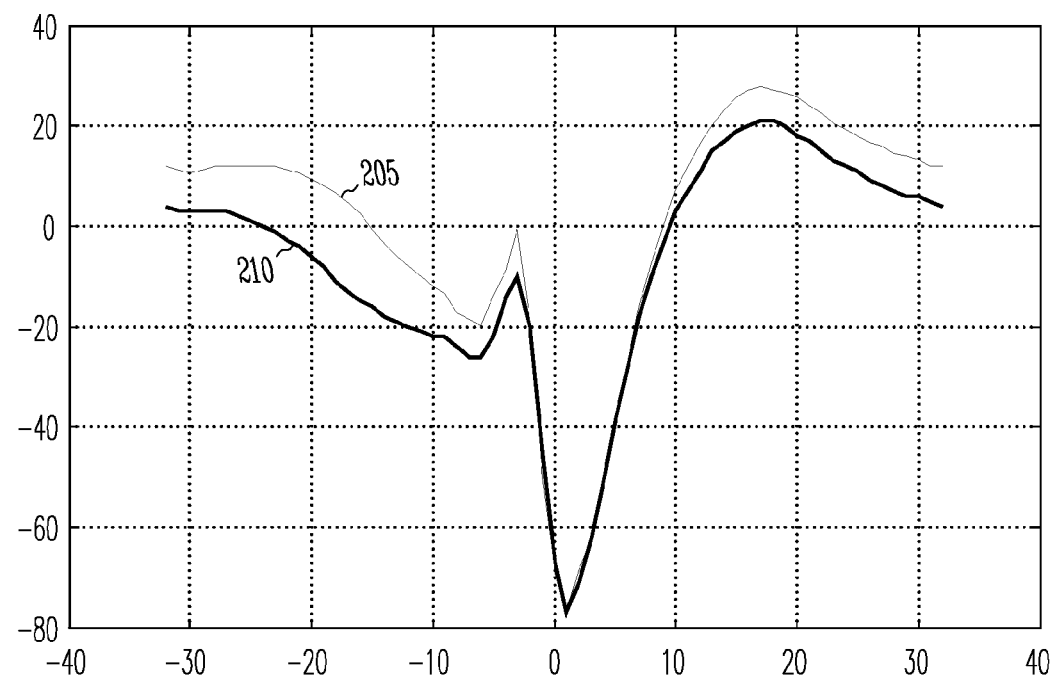
FIG. 2 illustrates an SVT template that has accurately captured a rate aberrant signal morphology.

FIG. 1 illustrates an example of an effect of a rate aberrant ventricular depolarization signal morphology 105 as compared to a normal sinus rhythm (NSR) ventricular depolarization template 110. Such a morphology difference between a rate-aberrant ventricular depolarization and the NSR template can affect the ability of a system to accurately identify rate-aberrant beat morphologies. By contrast, FIG. 2 illustrates an SVT template 210 that is more representative of a rate aberrant ventricular depolarization signal morphology 205. The present systems and methods may monitor or treat conditions using morphology-based tachyarrhythmia discrimination that is better able to handle rate aberrant beat morphologies.

Figure 3:
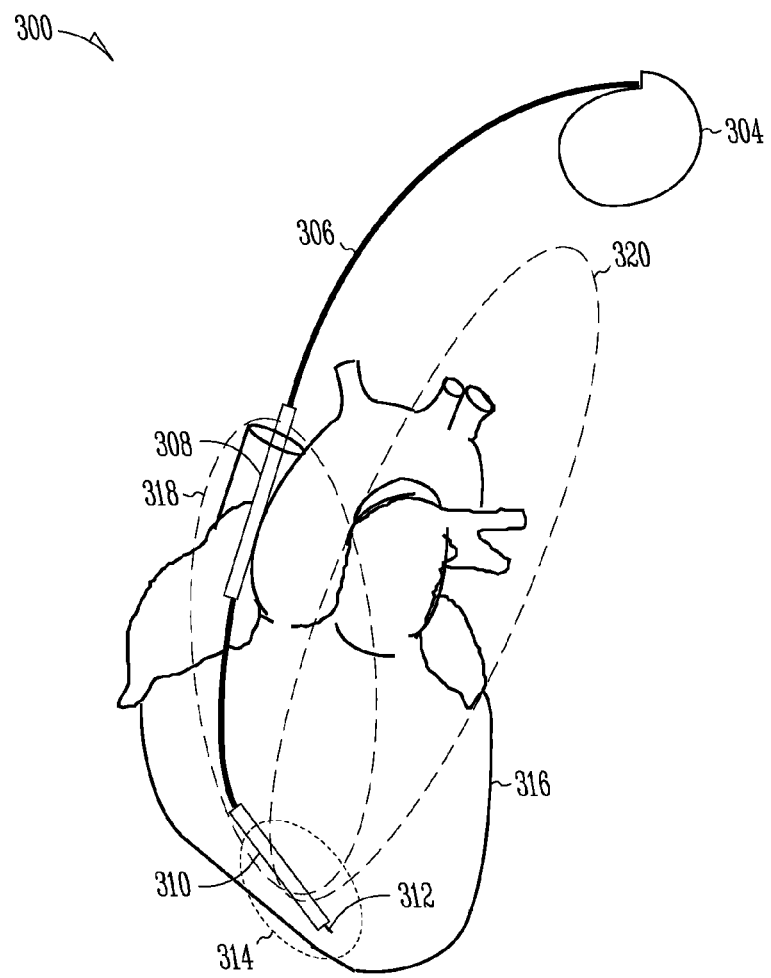
FIG. 3 illustrates portions of a system that uses a device for monitoring electrical signals of the heart.
Figure 3:
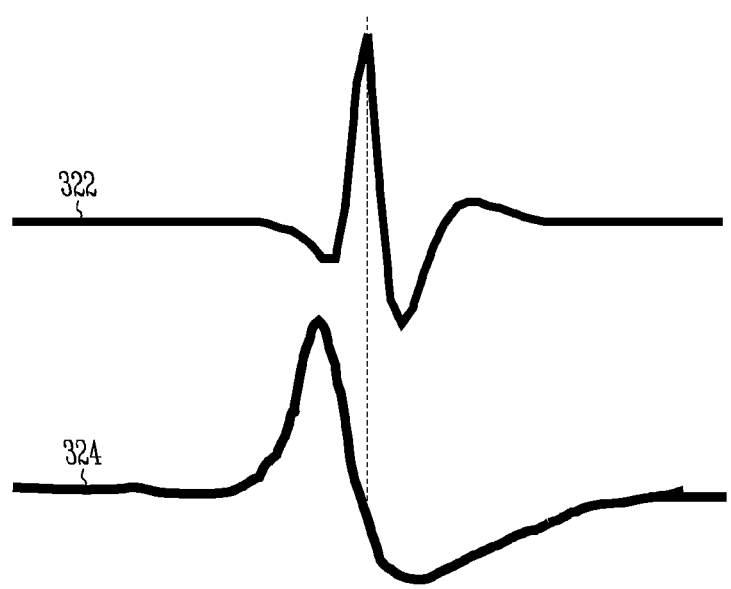

FIG. 3 illustrates portions of a system that uses a device 304 for monitoring one or more electrical signals of the heart 316. In certain examples, the device 304 is coupled to one or more lead wires 306 having a supraventricular (SV) coil electrode 308, a right ventricular (RV) coil electrode 310, and an RV tip electrode 312. An electrogram signal (EGM) is detected from intrinsic electrical signals occurring within the heart 316. In this example, there is more than one field in which the EGM signal may be obtained. A near-field 314 EGM is located between the RV tip electrode 312 and RV coil electrode 310. Far-field 318 and 320 EGMs can be respectively detected between (1) the SV coil electrode 308 and the RV coil electrode 310, (2) between the RV coil electrode 310 and an electrode located on the device 304, and (3) from the RV coil electrode 310 to a commonly-connected SV coil electrode 308 and an electrode that is provided by the conductive portion of device 304. The near-field 314 EGM is sometimes referred to as the rate channel 322 EGM. The far-field EGM 318 is sometimes referred to as the shock channel 324 EGM. The rate channel 322 EGM is sometimes used to provide a timing reference for the shock channel 324 EGM, as illustrated in FIG. 3, such as for temporally aligning the rate and shock channels.

In certain examples, the monitoring system uses information about a patient's prior tachyarrhythmia episode or episodes to improve tachyarrhythmia characterization and discrimination for the patient's later tachyarrhythmia episodes. In certain examples, the monitoring system uses information about a patient's prior episode to form one or more additional templates, capturing rate-aberrant or other different morphologies occurring during SVT to improve tachyarrhythmia discrimination.

As will be discussed below, the monitoring and treatment of an impending disease state can include first characterizing one or more tachyarrhythmia episodes. Later episodes can be characterized by comparing one or more beat morphologies during such later episodes to one or more beat morphology templates derived from prior episodes.

Examples

Figure 4:
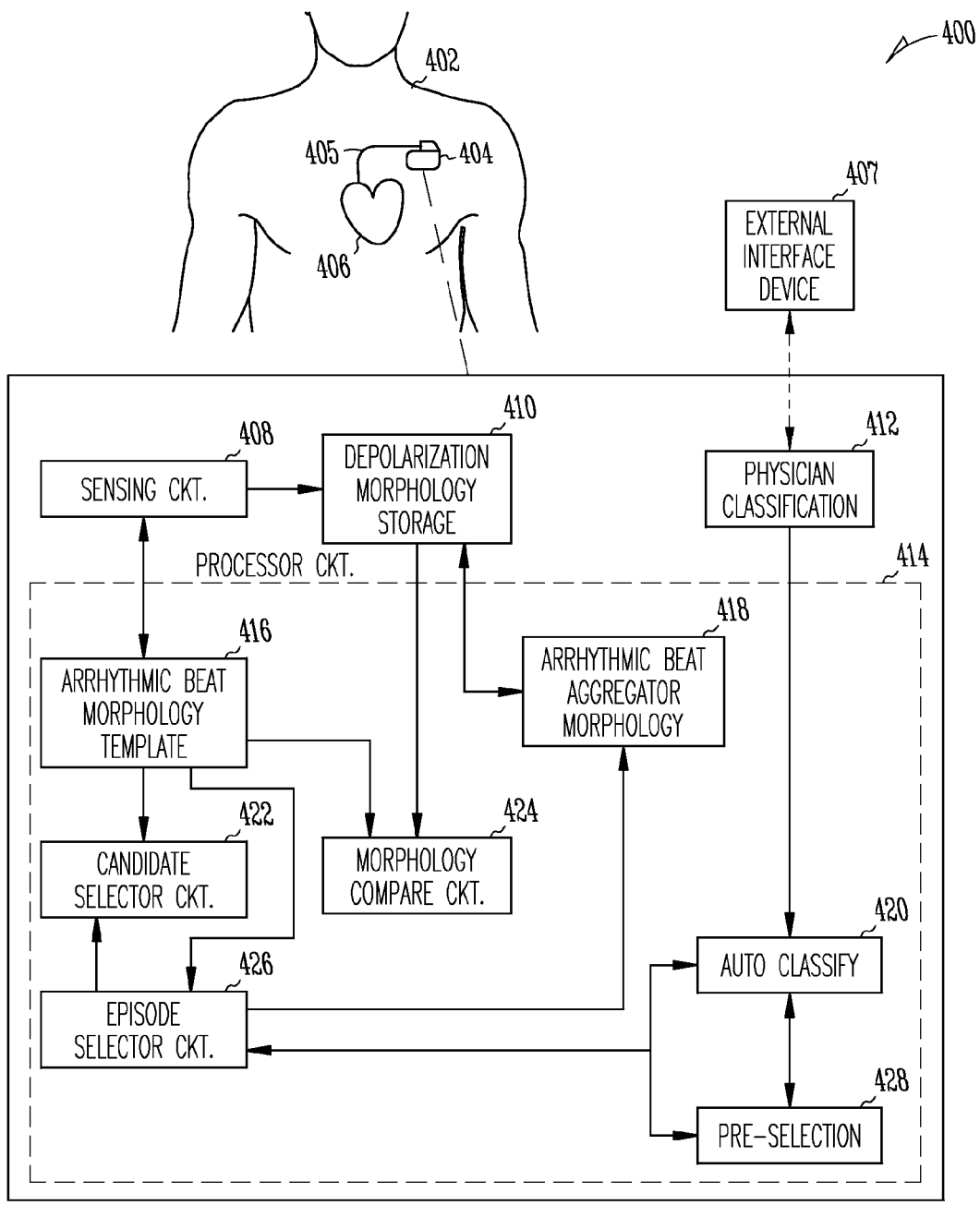
FIG. 4 is a schematic view illustrating one example of a system adapted to monitor one or more intrinsic electrical cardiac signals in a subject.

FIG. 4 is a schematic view illustrating generally one example of a portions of a system 400 adapted to monitor one or more intrinsic electrical cardiac signals in a subject 402 and an environment in which the system 400 may be used. As shown in FIG. 4, the system 400 may include an IMD 404, such as a CRM device, which can be coupled by at least one lead 405 or otherwise to a heart 406 of a subject 402. The IMD 404 may be implanted subcutaneously in the subject's chest, abdomen, or elsewhere. The system 400 can also include a local or remote external interface device 407, such as an external programmer or a remote server. The external interface device 407 can include a visual or other display, such as a LCD or LED display, for textually or graphically relaying information from the IMD 404 to a caregiver (e.g., a physician).

The IMD 404 typically includes a sensing circuit 408 such as to monitor one or more intrinsic electrical cardiac signals occurring in the subject 402. Morphological and other depolarization information from such intrinsic signals can be stored in a depolarization morphology storage circuit 410. Such depolarization morphology information can be used for comparing against candidate arrhythmic beats in a later-detected arrhythmia episode. For instance, if the system 400 initially detects an arrhythmia episode while sensing, the episode can be recorded in the depolarization morphology storage circuit 410 and may be used in forming or refining an arrhythmic beat morphology template to which later beats can be compared.

In certain examples, the system 400 further includes a processor circuit 414, which can be coupled to the depolarization morphology storage circuit 410, and an arrhythmic beat morphology template 416, which typically represents morphological features of a depolarization characteristic of a particular arrhythmia. The processor circuit 414 can include a candidate arrhythmic beat selector circuit 422 for selecting at least one candidate arrhythmic beat for use in forming the arrhythmic beat morphology template 416. In certain examples, the candidate arrhythmic beat selector circuit 422 uses information obtained from comparing the cycle interval, beat amplitude or rate zone classification of at least two candidate arrhythmic beats from one or more arrhythmia episodes. The cycle interval represents the period of time between repeated events such as the time between P waves (e.g., upper heart chamber electrical activity typically occurring once during each heart beat) or the time between R waves (e.g., lower heart chamber electrical activity typically occurring once during each heart beat). Rate zone classification may be used when a CRM classifies more than one heart rate based upon one or more known threshold rate values or ranges.

The processor circuit 414 can also include a beat morphology aggregator circuit 418 to form the arrhythmic beat morphology template 416, such as by combining depolarization morphology information from at least two candidate arrhythmic beats. A beat morphology comparator circuit 424 is configured to determine an indication of a similarity, such as between depolarization morphology information of a later beat (e.g., after template formation) and the arrhythmic beat morphology template 416. The beat morphology comparator circuit 424 is adapted to classify the later beat using the determined similarity. If a subject's condition changes over time, the beat morphology template is updated to reflect such changes, thereby increasing the accuracy of classifying beats using the template.

In FIG. 4, an arrhythmia episode selection circuit 426 is configured to select at least one arrhythmia episode to be used by the candidate arrhythmic beat selector circuit 422, for selecting at least one candidate arrhythmic beat from the selected arrhythmia episode. The beat morphology aggregator circuit 418 can further use the selected arrhythmia episode for template formation. An automatic arrhythmia classification circuit 420 is adapted to form an automatic classification of an arrhythmia type of the arrhythmia episode selected by the arrhythmia episode selection circuit 426, such as by using input derived from a received physician classification 412 of an arrhythmia type of the arrhythmia episode. In certain examples, the physician classification of arrhythmia episodes uses a display panel to illustrate the depolarization waveforms during the various arrhythmia episodes to allow the physician to label each episode as a VT or a SVT. Labeled episodes may be used to either form or adjust the arrhythmic beat morphology template 416.

Potential arrhythmic beat morphology template 416 beats can be chosen from one or more stored episodes for which therapy has been delivered. The physician may then review some or all of the stored episodes and label the episodes as SVT or VT. The episodes can also be automatically sorted or prioritized, such as described below in reference to FIG. 5.

In FIG. 4, a pre-selection circuit 428 is adapted to pre-select one or more beats within the arrhythmia episode, such as for use in forming an arrhythmic beat morphology template 416 to represent that arrhythmia episode. The pre-selection circuit 428 may be configured to select one or more beats to be used by the automatic arrhythmia classification circuit 420. In an example, one or more beats associated with an onset of the arrhythmia episode are selected, such as an episode identified as an SVT by the device, which correlates to a physician's annotation. In another example, one or more beats deemed morphologically different from a NSR morphology are selected, such as beats occurring in a true SVT episode which do not correlate well against a normal sinus rhythm (NSR) beat morphology template.

Figure 5:
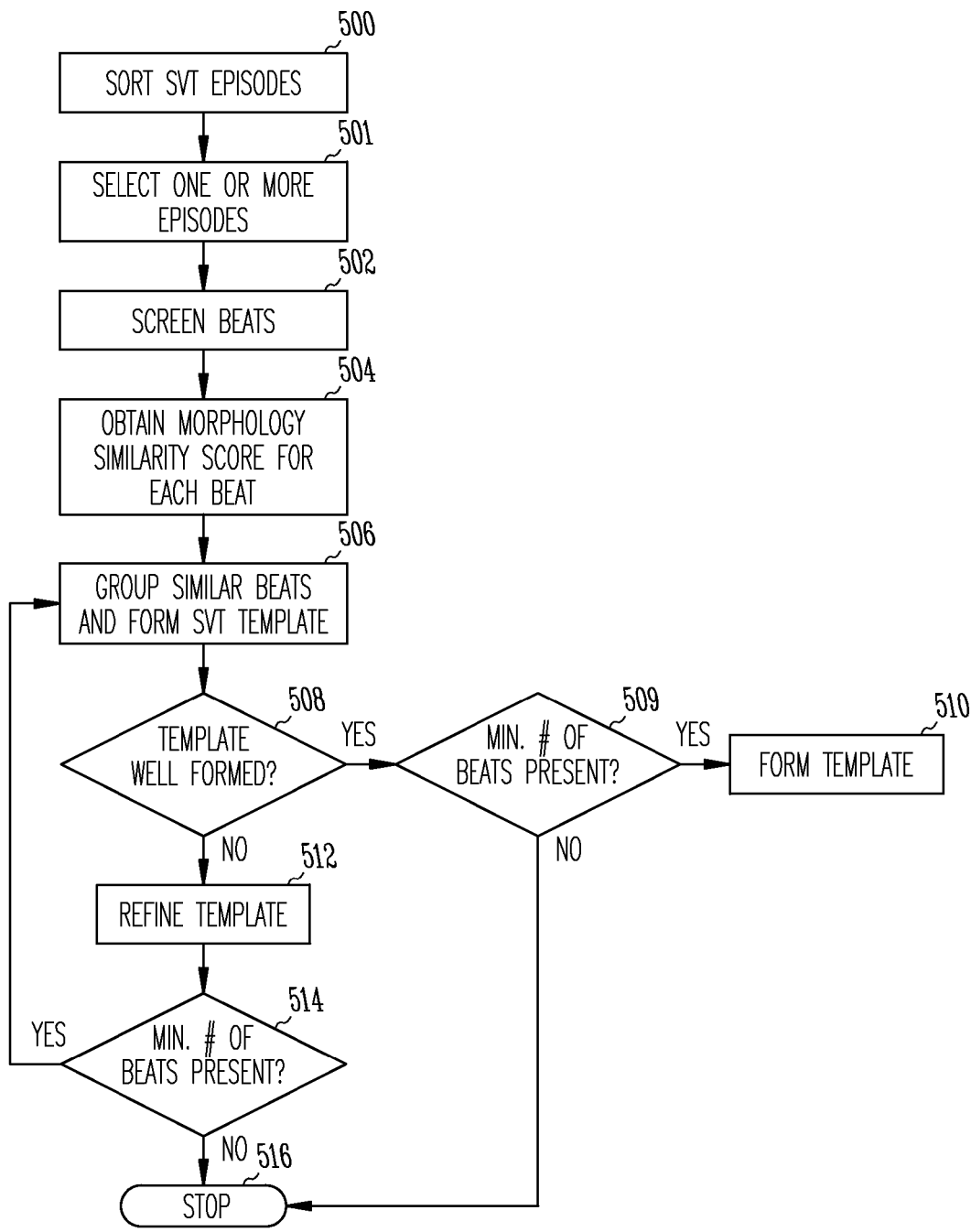
FIG. 5 illustrates one example of sorting or prioritizing arrhythmia episodes, such as for use in forming or adjusting an arrhythmic beat morphology template.

FIG. 5 illustrates one example of sorting or prioritizing arrhythmia episodes, such as for use in forming or adjusting an arrhythmic beat morphology template. At 500, episodes annotated as SVT by a physician are sorted based on one or more pre-defined criteria, such as by time of occurrence, or by whether an automatic classification by the system 400 matches the physician annotation. Examples of different sorting options are described below with respect to FIG. 7. At 501, one or more of the annotated episodes is selected as one or more candidate episodes from which beats can be selected for use in forming the SVT template. At 502, the beats are screened, such as to eliminate any outlier beats that might reduce the accuracy of a morphology template formed using such outlier beats. Various screening options are described in more detail below with respect to FIG. 6. At 504, a morphology similarity score is obtained. This can include calculating an autocorrelation score (or other similarity indication) for pairs of beats to find morphologically similar beats among those that remained after 502. At 506, similar beats are grouped together, such as by using the similarity scores of 504. In an example, the group having the largest number of member beats is used to form the SVT template as a composite of such member beat morphologies. Combining the member beat morphologies can involve averaging them together, for example. In another example, the groups are ranked according to the similarity score of their member beats and one or more other criteria (such as the most recent beat) is used to determine which group is selected to form the SVT template. In this manner, a highly similar beat morphology, occurring immediately prior to therapy delivery, may have first priority.

At 508, the template is confirmed. Such confirmation can involve correlation of the morphology of each beat used to create the template to the morphology of the resulting template. A high similarity score between the resulting template and the morphologies of the beats used to create the template can be used to confirm the validity of the template. In an example, the beats used in forming the template may be compared against the template itself in order to validate the template. In an example, a minimum of twenty beats (for example) may be desired to form a template and if only nineteen or less meet the similarity score comparison and are grouped for template formation, the template may not be formed. At 509, the specified minimum number of beats is checked against the current group of beats to be used in the formation of the template. If the specified threshold for minimum number of beats is met or exceeded, at 510, the confirmed template is stored for later use by the device in detecting or classifying later arrhythmias. Otherwise the process stops at 516. At 512, if the similarity score indicates that the template does not adequately represent the beats from which it was formed, then such template may benefit from refinement. In an example, the beat having the lowest similarity score of the group to the template is removed, and the template is reformed and again confirmed, as described above. This may involve repeated attempts to confirm a valid template, and may not result in a valid template, such as if an insufficient number of beats remain after refinement. At 514, the number of beats used to form the template is compared to a specified threshold value. The threshold value specifies a minimum number of beats needed to form an acceptable template. In an example, at 512, certain beats were removed and the number of remaining beats may only comprise that which is contained in a single episode, allowing for one selected episode to be used in refining the template. The minimum number of beats may be determined a number of different ways such as if too few beats exist in the episode to consider it reliable. In such an example, it may be best to advance to 516 and stop further verification of the SVT template. The confirmed SVT template can be compared to other stored SVT and VT episodes. If the template has high correlation to a VT episode or does not adequately correlate with any SVT episodes, it may be discarded (again moving to 516).

Figure 6:
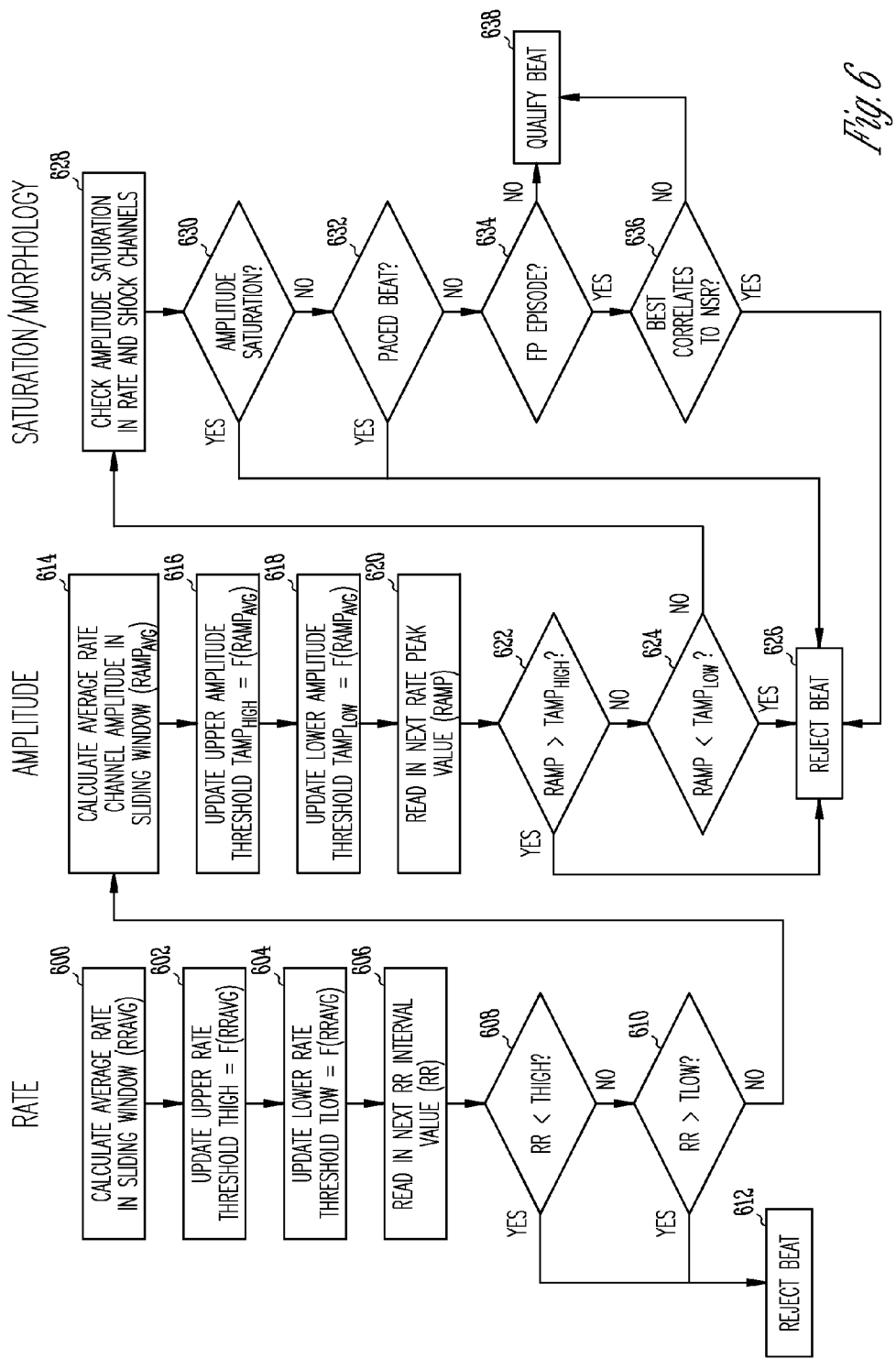
FIG. 6 illustrates an example of different criteria for screening beats from one or more selected episodes.

FIG. 6 illustrates examples of one or more different criteria for screening beats from one or more selected arrhythmia episodes. Electrocardiography (EKG, ECG) or electrogram tracings show a characteristic pattern of electrical impulses that are generated by the heart, such as that illustrated in FIG. 1. One part of the electrical impulse, called the QRS complex, is a record of the measurement of the movement of electrical impulses through the lower heart chambers, or ventricles. The peak of the QRS complex is known as an 'R' wave and the time interval between two R waves is a measure of heart rate (e.g., R-R value). In an example, a fixed period of time, referred to as a window, is placed at the beginning of an episode having candidate beats. The window may be wide enough in time to capture two or more candidate beats sufficient to calculate an average R-R value. This window may be shifted later in time, with respect to the beginning of the episode and with each subsequent beats falling within the window, a new R-R value is calculated. This allows the continual updating of the stored R-R value with new data which may then be compared against a threshold range of an upper and lower R-R value. At 600, an average (or other central tendency of) R-R value is calculated over a first referenced window, containing a specifiable number of beats. This central tendency of R-R value may include a mean, median value, or weighted average representative of a group of depolarizations. At 602, an upper rate interval threshold ($T_{high}$) is determined as a function of the calculated R-R value from the first referenced window which may represent the shortest preferred threshold. At 604, the lower rate interval threshold ($T_{low}$) is determined as a function of the calculated R-R value which may represent the longest preferred threshold. At 606, the next R-R value (e.g., R-R value adjusted in time when a fixed window of beats is moved within an episode) in an arrhythmia episode is analyzed. At 608, this R-R value is first checked to see if it is shorter than $T_{high}$. If so, then at 612, the beat is rejected from those to be used in template formation. If however, the next R-R value is longer than $T_{high}$, at 610, the next R-R value is checked to see if it is longer than $T_{low}$ and if so, at 612, the beat is rejected from those to be used in template formation. In the event that this R-R value falls between both $T_{high}$ and $T_{low}$, at 614, one or more amplitude criteria is checked.

At 614, an average (or other central tendency of) rate channel amplitude ($R_{Amp}$) is calculated within the window or to include a specifiable number of beats. This average or other central tendency $R_{Amp}$ may include a mean, median value, or weighted average representative of a group of depolarizations. At 616, an upper amplitude threshold ($R_{Amp,high}$) is determined as a function of the calculated $R_{Amp}$, which may represent the highest allowable amplitude for template formation. In an example, the $R_{Amp,high}$ may be represented as a percentage above the first referenced $R_{Amp}$. At 618, a lower amplitude threshold ($R_{Amp,low}$) is calculated within the window or to include a specifiable number of beats, which may be represented as a percentage below the first referenced $R_{Amp}$. At 620, the next $R_{Amp}$ (e.g., $R_{Amp}$ value adjusted in time when a fixed window of beats is specified and moved within an episode) is analyzed to first determine if it is below $R_{Amp,high}$, at 622, and if so, at 626, the beat is rejected from those to be used in template formation. If however, the next $R_{Amp}$ is greater than $R_{Amp,high}$, at 624, the next $R_{Amp}$ is checked to see if it is above $R_{Amp,low}$, and if so, the beat is rejected, at 626. In the event that the next $R_{Amp}$ falls between both $R_{Amp,high}$ and $R_{Amp,low}$, then, at 628, one or more saturation/morphology criteria are checked.

At 628, the amplitude of the signal is checked for saturation (e.g., exceeding a maximum amplitude threshold or clipping of the signal). At 630, if amplitude saturation is present, the beat is rejected, at 626. If, however, there is no amplitude saturation present, then at 630, the signal is checked to determine whether the beat is a paced beat, at 632, and if so, the beat is rejected at 626. If not a paced beat, at 632, the beat is checked, at 634, to determine if it is originating from a false positive (FP) detected episode. A FP episode may be present if a physician annotates an episode as an SVT which was not classified as such by the device automatic arrhythmia classification. If the beat is not from a FP episode, the beat is qualified, at 638. A qualified beat represents a beat which has not been rejected and may be used in template formation. If, at 634, beats are from a FP episode, then the beats are correlated against a NSR beat morphology template, at 636. If at 636, similarity to an NSR beat is determined, at 626, the beat is rejected from those to be used in template formation, otherwise, at 638, the signal beat is qualified to be used in template formation. If multiple episodes are used and they include at least one FP and true negative episodes, the beat correlation, at 636, may be used to screen all beats within the multiple episodes, selecting those that are not correlated to an NSR template as qualified at 638. However, in the absence of at least one FP episode, among the multiple episodes, all beats within the multiple episodes may be selected as qualified, at 638.

Figure 7:
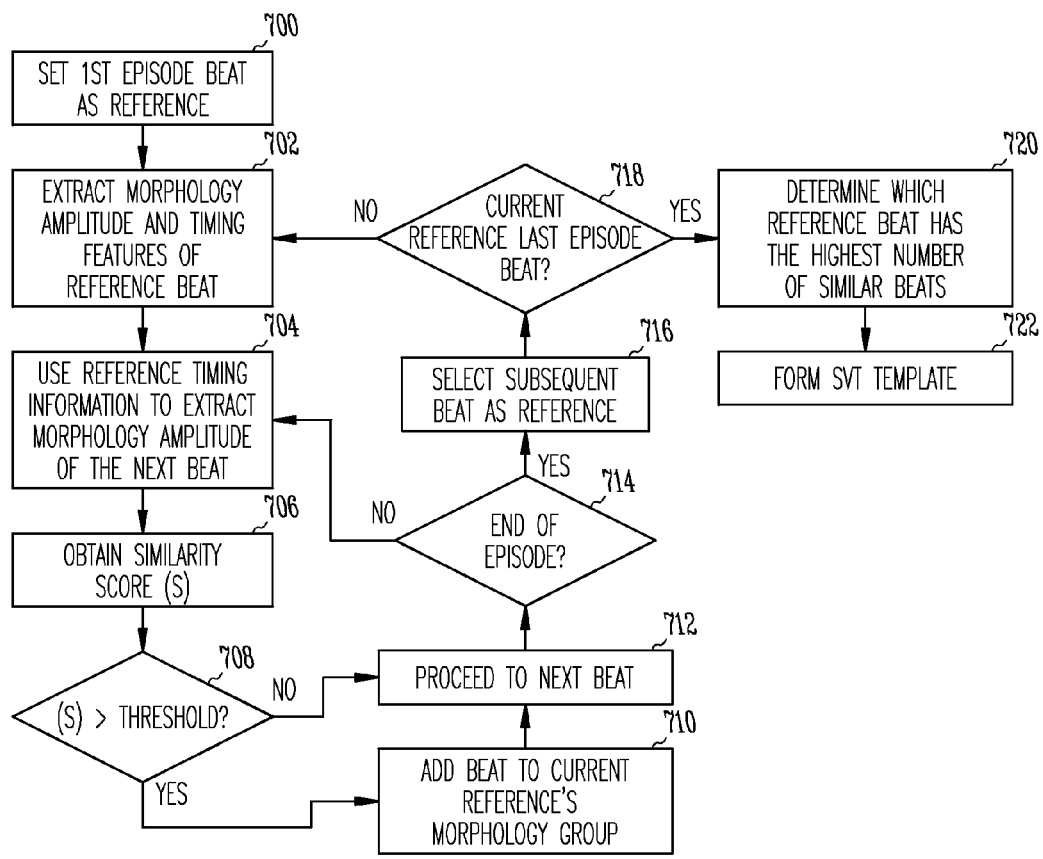
FIG. 7 illustrates an example of beat selection.
Figure 8:
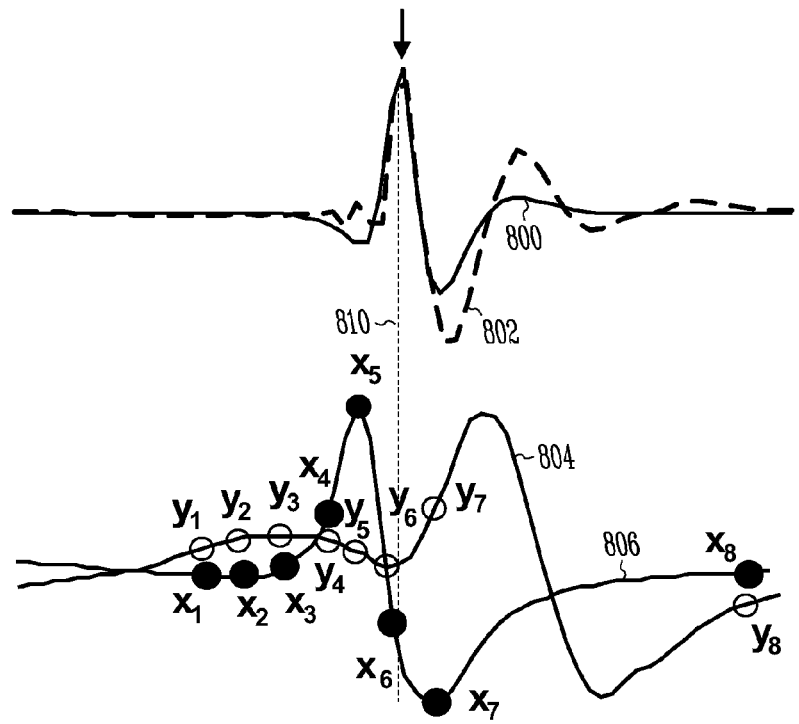
FIG. 8 illustrates the use of feature correlation coefficient (FCC) to determine a similarity score between beats.

FIG. 7 illustrates an example of beat selection. At 700, a beat is set as a reference beat (e.g., the first beat). At 702, morphology amplitude and timing features are determined from the reference beat. Amplitude and timing features may be determined using feature correlation coefficient (FCC) methods described in FIG. 8 below. At 704, the timing information is used to determine morphology amplitude of the next beat occurring in time after the reference beat. The feature point of the reference beat is matched in timing, adjusted for beat position, to the next beat as described in FIG. 8 below. At 706, a similarity score (S) is calculated, such as illustrated in FIG. 8. At 708, the similarity score S is checked to see if S is greater than a predetermined threshold. If so, at 710, this beat is added to a current reference beat morphology group comprising accrued reference beats to become one of the beats used in template formation. Otherwise, at 712, the process proceeds to the next beat occurring in time within the arrhythmia episode being evaluated. If, at 714, the next beat results in the end of the arrhythmia episode, at 716, a new beat is selected as a reference. For example, the beat following the current reference is compared to all others in the episode. Otherwise, at 704, the reference timing information is used to determine the morphology amplitude of the next beat. In this manner, each beat is successively evaluated as a reference beat. At 718, the current reference is checked to determine whether it constitutes the last beat of the arrhythmia episode or episodes being analyzed. If so, at 720, it is determined which reference beat is similar to the highest number of other beats. Otherwise, at 702, morphology amplitude and timing features are determined from the reference beat. At 722, the SVT template is formed by averaging the beats within the morphology group having the highest number of similar beats.

It is expected that updated rhythm analysis results may be presented to a physician to review and validate the SVT template formed at 722. In certain examples, the physician may view episodes newly classified by the SVT template, formed at 722, to determine if arrhythmia episodes are properly classified. This may be performed similarly as described in FIG. 4 using external interface device 407. It is expected that remote access by the physician may be used, thereby allowing the physician to make such determination without being physically close to the patient. In certain examples, the physician, either locally or remotely, may annotate the diagnosis for each rhythm first classified by the IMD 404 as a VT as being a true positive or FP and subsequently the system may determine if any true positive episodes have been reclassified as SVTs while utilizing the new template.

FIG. 8 illustrates an example of using a FCC to determine a similarity score between reference beat features, such as those within an SVT template, and beat features which have been identified as candidate beats to be classified or incorporated into a refined SVT template. It is anticipated that various reference beats may be utilized, such as those from a NSR template. In this example, there are a total of eight features to be compared. If a different number of features is desired, the number eight may be replaced by the total number of features to be correlated. A reference beat 800 is compared against a subsequent beat 802, which are temporally aligned along a fiducial mark 810, according to a known feature such as a peak of the QRS complex. An example of feature selection is described in Kim et al. U.S. Pat. No. 6,708,058, entitled "NORMAL CARDIAC RHYTHM TEMPLATE GENERATION SYSTEM AND METHOD", issued on Mar. 16, 2004, which is incorporated by reference in its entirety, including its description of a FCC and its use in forming a normal sinus rhythm (NSR) template. Signals 804 and 806 show more separation of the signals to be compared with the features identified. The data points labeled in the $X_i$ coordinates represent template features, which coincide in time with $Y_i$ coordinates and are used in the equation 808. The sign of the numerator term is checked before squaring to determine if a negative numerator exists. If so, the beat is uncorrelated and the remainder of the equation need not be completed. If a positive numerator exists, a similarity score results and may then be compared to a specified FCC threshold.

Figure 9:
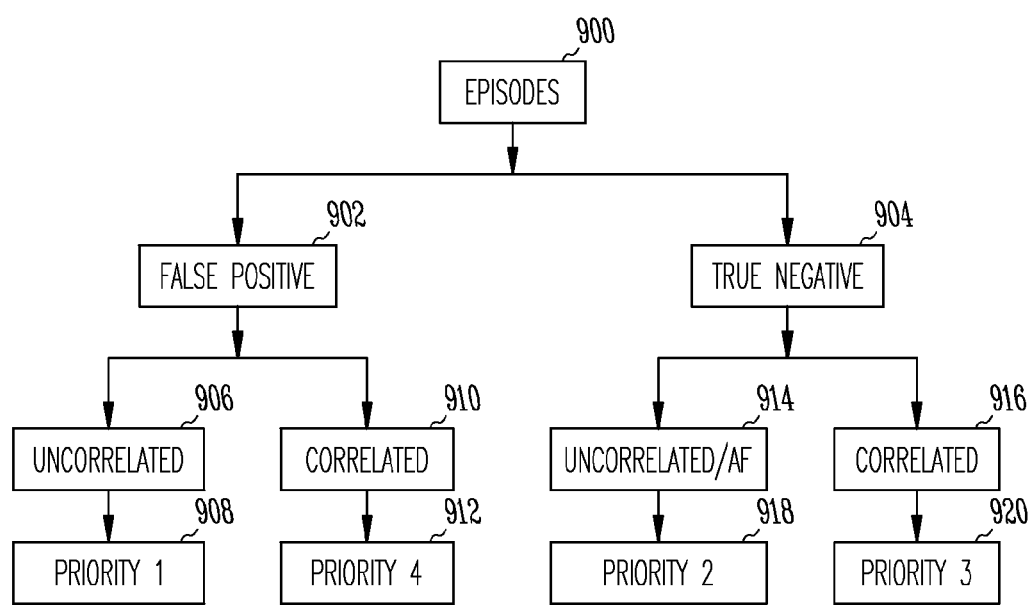
FIG. 9 illustrates generally an example of portions of a technique for sorting or prioritizing arrhythmia episodes for use in forming or refining an arrhythmic beat morphology template.

FIG. 9 illustrates generally an example of portions of a technique for sorting or prioritizing arrhythmia episodes for use in forming or refining an arrhythmic beat morphology template. At 900, physician-annotated arrhythmia episodes are sorted into at least two categories: false positive 902 or true negative 904. In an example, a false positive 902 exists if the physician's annotation does not match the automatic arrhythmia classification of the device (e.g., the device misclassified an arrhythmia as an SVT), and a true negative 904 exists if the physician's annotation matches the automatic device classification of the episode (e.g., both identified as SVT). A false positive 902 may generally be a good candidate episode as a basis for forming a new arrhythmic beat morphology template, because future beats that match such a template will avoid future false positives.

In an example, a dual chamber device is used, and further sorting is performed. Such sorting may give higher priority to forming an arrhythmia morphology template from arrhythmia episodes that are uncorrelated 906 and/or which are labeled by the device to have unstable ventricular rhythm accompanied by a fast atrial rate (AF) 910. An episode that is uncorrelated 906 may represent a true SVT episode which was improperly classified as a VT episode through morphological comparison or that the beats of interest in an episode do not match a NSR template, and may be rate aberrant. A priority can be assigned to each type of condition for use in determining which arrhythmia episodes will be most useful for template formation or reformation. For example, uncorrelated 906 arrhythmia episodes can be given classification of priority 1 at 908 and correlated false positives can be given a priority 4 at 912. One example of correlated false positives are SVT episodes mislabeled as VT by the fact that the ventricular rate appeared to exceed the atrial rate (V>A). Further prioritization of episodes can be performed, such as within priority 1 908. Similarly, other prioritization of episodes can be performed, which may include giving higher priority to episodes occurring most recently in time. The prioritizations can be combined into a composite prioritization, such as by weighting the individual prioritizations, as desired.

Similarly, true negative 904 classification may benefit from further classification of the episode, such as to uncorrelated/AF 914 or correlated 916. Uncorrelated/AF 914 may represent episodes that are not similar to the NSR template but in which the episodes were identified by an atrial fibrillation sense module (AF module) to be SVT. Correlated 916 may include an episode which is similar the NSR template. In an example, a priority can be assigned to these further classifications, such as priority 2 at 918 (e.g., giving greater priority for uncorrelated/AF 914 than that of V>A 910 of a false positive 902 episode) and priority 4 at 920 (e.g., lowest priority) to a correlated episode at 916. Other combinations of classifications can similarly be used for such prioritization.

Figure 10:
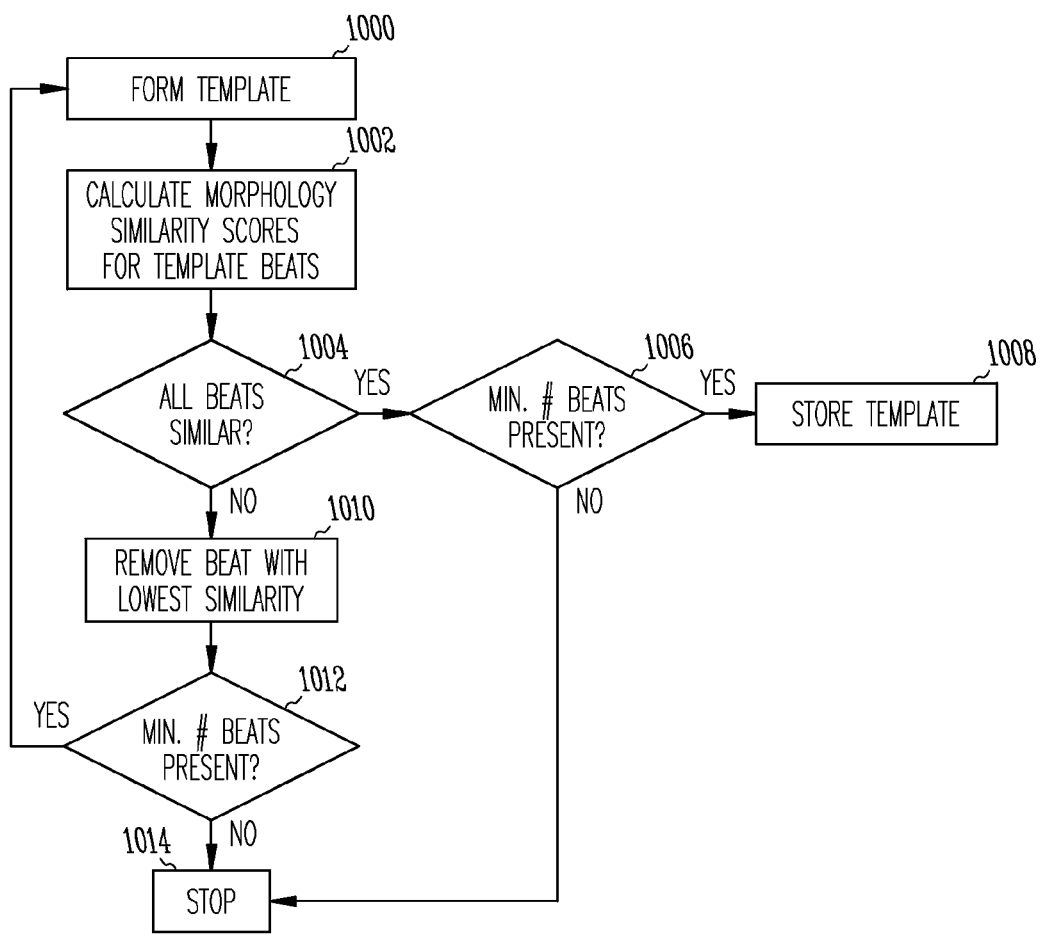
FIG. 10 shows one example of refining a template that has been formed.

FIG. 10 illustrates an example of refining a template, which has been formed. At 1000, the template formation has occurred. At 1002, similarity scores are calculated for template beats (e.g., beats that were used to form the template). At 1004, a check is performed for all beats having high similarity to a reference beat. If all beats that were used to form the template exhibit a high enough similarity to the reference beat, then, at 1006, a check is performed to ensure that the template was formed from at least a minimum number of beats, as compared to a specified threshold number of beats. If not, then at 1014, template refinement is stopped. If, however, at 1006 the minimum threshold is met, then, at 1008, the template is stored. If, at 1004, the beats were not significantly similar to the reference beat, then, at 1012, the beat having the lowest similarity score established at 1002 is removed, and a check for a specified minimum number of beats present is performed. If, at 1012, a specified threshold for minimum number of beats is met, the template is reformed, at 1000, after the lowest beat is removed, otherwise, at 1014, template refinement is stopped.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:
1. A method for discriminating arrhythmias, comprising:
   selecting one or more arrhythmia episodes of an arrhythmia type from a plurality of arrhythmia episodes;
   screening beats of the one or more arrhythmia episodes using specified criteria;
   determining morphology similarity scores each between two beats of the screened beats, including calculating a correlation between the two beats;
   selecting beats from the screened beats using the morphology similarity scores; and forming an arrhythmic beat morphology template for the arrhythmia type using the selected beats.

2. The method of claim 1, further comprising:
determining a similarity between a beat and the arrhythmic beat morphology template after the formation of the arrhythmic beat morphology template; and
classifying the beat using the similarity.

3. The method of claim 1, wherein selecting the beats comprises:
grouping the screened beats into groups of morphologically similar beats using the morphology similarity scores; and
selecting a group having a largest number of the morphologically similar beats.

4. The method of claim 3, wherein forming the arrhythmic beat morphology template comprises averaging the morphologically similar beats of the selected group.

5. The method of claim 3, wherein selecting the beats comprises:
ranking the groups using the morphology similarity scores and one or more additional criteria; and
selecting a group using the ranking of the groups.

6. The method of claim 1, further comprising confirming validity of the arrhythmic beat morphology template using a similarity between the arrhythmic beat morphology template and morphologies of the beats selected to form the arrhythmic beat morphology template.

7. The method of claim 6, wherein forming the arrhythmic beat morphology template comprises forming the arrhythmic beat morphology template for the arrhythmia type using the selected beats if the number of the selected beats exceeds a specified minimum number.

8. The method of claim 1, wherein selecting the one or more arrhythmia episodes of the arrhythmia type comprises:
performing automatic classifications of episodes of the plurality of arrhythmia episodes;
receiving physician classifications of the episodes of the plurality of arrhythmia episodes; and
comparing the automatic classifications to the physician classifications.

9. The method of claim 8, further comprising reviewing and validating the formed arrhythmic beat morphology template by a physician.

10. The method of claim 1, wherein forming the arrhythmic beat morphology template for the arrhythmia type comprises forming an arrhythmic beat morphology template for supraventricular tachyarrhythmia (SVT).

11. A method for discriminating arrhythmias, comprising:
classifying at least one arrhythmia episode as an arrhythmia type, the at least one arrhythmia episode including a plurality of beats;
determining morphology similarity scores each between a two beats of the plurality of beats;
grouping beats of the plurality of beats into one or more groups of morphologically similar beats using the morphology similarity scores;
selecting a group from the one or more groups; and
forming an arrhythmic beat morphology template for the arrhythmia type using the selected group.

12. The method of claim 11, further comprising:
determining a similarity between a beat of a further arrhythmia episode and the arrhythmic beat morphology template after the formation of the arrhythmic beat morphology template; and
classifying the beat of the further arrhythmia episode using the similarity.

13. The method of claim 12, wherein forming the arrhythmic beat morphology template for the arrhythmia type comprises forming an arrhythmic beat morphology template for supraventricular tachyarrhythmia (SVT).

14. The method of claim 12, wherein selecting the group comprises selecting a group having a largest number of the morphologically similar beats.

15. The method of claim 12, wherein selecting the group comprises:
ranking the one or more groups using the morphology similarity scores and one or more additional criteria; and
selecting the group using the ranking of the one or more groups.

16. The method of claim 11, wherein forming the arrhythmic beat morphology template comprises averaging the morphologically similar beats of the selected group.

17. The method of claim 11, wherein classifying the at least one arrhythmia episode comprises classifying an arrhythmia episode as the arrhythmia type by a physician.

18. The method of claim 17, the classifying the arrhythmia episode as the arrhythmia type by the physician comprises:
displaying to the physician depolarization waveforms of the at least one arrhythmia episode;
receiving from the physician a physician classification made upon viewing the displayed depolarization waveforms, the physician classification labeling the at least one arrhythmia episode as the arrhythmia type being one of known arrhythmia types.

19. The method of claim 18, wherein classifying the at least one arrhythmia episode comprises:
performing an automatic classification of the at least one arrhythmia episode;
receiving the physician classification of the at least one arrhythmia episode; and
comparing the automatic classification to the physician classification.

20. The method of claim 19, further comprising reviewing and validating the formed arrhythmic beat morphology template by the physician.

* * * * *